United States Patent [19]

Gartz

[11] Patent Number: 5,084,019

[45] Date of Patent: Jan. 28, 1992

[54] HYPODERMIC SYRINGE WITH MEANS TO DESTROY AND SAFELY STORE THE CANNULA

[75] Inventor: Kaj Gartz, Orange, Conn.

[73] Assignee: Owen J. Meegan, Salem, Mass. ; a part interest

[21] Appl. No.: 657,529

[22] Filed: Feb. 19, 1991

Related U.S. Application Data

[63] Continuation-in-part of Ser. No. 621,287, Nov. 30, 1990.

[51] Int. Cl.⁵ .............................................. A61M 5/00
[52] U.S. Cl. .................................... 604/110; 604/192; 604/240
[58] Field of Search ............... 604/110, 162, 167, 192, 604/195, 198, 240, 243, 263; 239/195, 198; 43/20

[56] References Cited

U.S. PATENT DOCUMENTS

| | | | |
|---|---|---|---|
| 3,419,992 | 1/1969 | Strahm | 43/20 |
| 3,472,456 | 10/1969 | Strong | 239/198 |
| 3,747,812 | 7/1973 | Karman | . |
| 3,893,608 | 7/1975 | Koenig | . |
| 4,026,287 | 5/1977 | Haller | 604/195 |
| 4,266,544 | 5/1981 | Wardlaw | . |
| 4,273,123 | 6/1981 | Lemelson | . |
| 4,428,139 | 1/1984 | Henze et al. | 43/20 |
| 4,582,257 | 4/1986 | Siegler | 239/198 |
| 4,634,428 | 1/1987 | Cuu | . |
| 4,804,370 | 2/1989 | Haber et al. | 604/110 |
| 4,907,600 | 3/1990 | Spencer | 604/240 |
| 4,925,450 | 5/1990 | Imonti et al. | 604/204 |
| 4,932,939 | 6/1990 | Magre et al. | 604/195 |
| 4,978,340 | 12/1990 | Terrill et al. | 604/110 |
| 4,986,813 | 1/1991 | Blake et al. | 604/195 |
| 5,019,048 | 5/1991 | Margolin | 604/240 |

FOREIGN PATENT DOCUMENTS

2634651 2/1990 France .............................. 604/192
8911304 11/1989 World Int. Prop. O. .

Primary Examiner—C. Fred Rosenbaum
Assistant Examiner—Sharon Finkel
Attorney, Agent, or Firm—Owen J. Meegan

[57] ABSTRACT

A hypodermic syringe having a cannula with a point that can be safely destroyed and stored. A portion of the cannula is disposed within a hollow housing that has a reel fitted therein and a portion extends externally therefrom through an aperture in which it is slidably received. A portion of the cannula is disposed in the reel whereby to enable a user to turn the reel, wrap the cannula around the reel to destroy and store it. When the point is fully retracted into the housing, the point can snap against the inside of the housing and provides sensory indications that it is fully withdrawn. The axis of rotation of the reel is at right angles to the cannula.

21 Claims, 2 Drawing Sheets

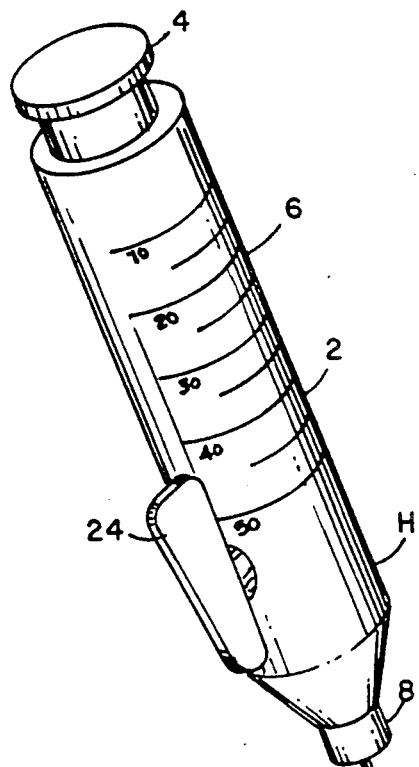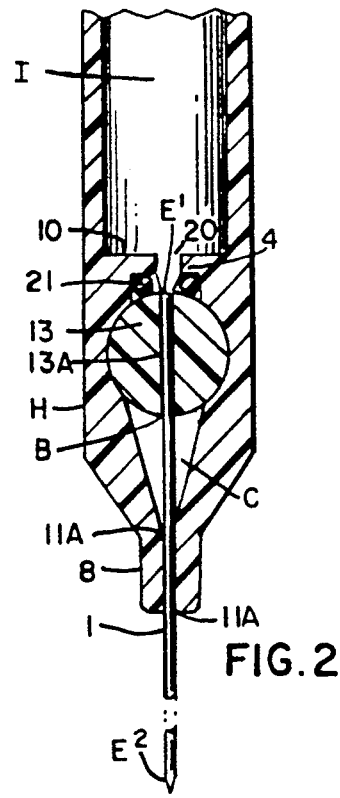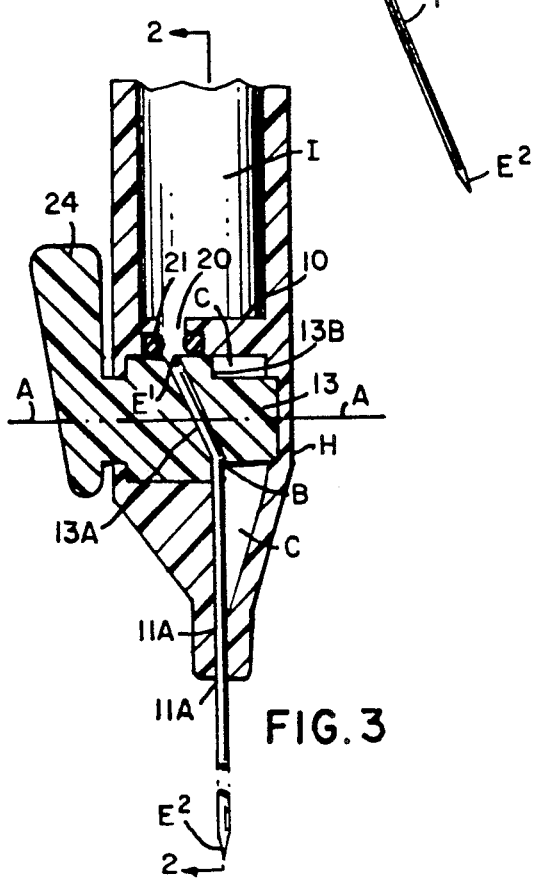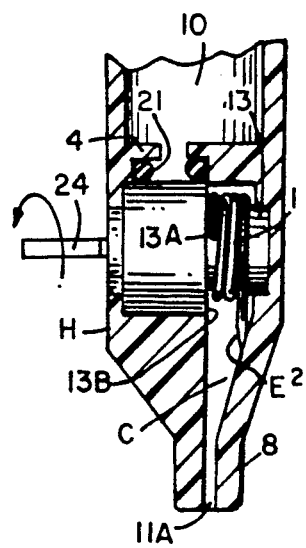
FIG.1
FIG.2
FIG.3
FIG.4

HYPODERMIC SYRINGE WITH MEANS TO DESTROY AND SAFELY STORE THE CANNULA

RELATED CASES

This application is a continuation in part of my co-pending application, Ser. No. 621,287 filed Nov. 30, 1990.

BACKGROUND OF THE INVENTION

The present invention relates to a device for the safe destruction and storage of used cannulas and especially the safe destruction and storage of cannulas of hypodermic syringes suitable for sampling blood or injecting therapeutic medications and are adapted to be used only once.

Cannulas and equipment used for injecting therapeutic fluids frequently are disposable and designed to be discarded after a single use. Once a cannula has been used to inject a medication, it is contaminated. The sharp point on a contaminated needle can injure people in that it cause the spread of disease among those that handle it. Infectious diseases such as HIV or hepatitis viruses have been transmitted to people who handle contaminated needles and accidentally stick themselves with them. Small residues of blood and viruses on the cannula from an infected patient can result in transmission of a disease that the patient has contracted to a staff member.

In the past, relatively complex arrangements have been devised to prevent the accidental infections from contaminated needles. I have found that covering of sharp points and destruction of the cannulas to prevent reuse is highly desirable because hypodermic needles are frequently reused by drug abusers and accidental contact or intentional use must be eliminated.

Exemplary of devices which have attempted to solve these problems is the application of Ameur: Int Pub. No. WO89/11304; PTC/SE89/00290. The application discloses a pair of protective sleeves that are displaceable in a longitudinal direction over a holder that is provided for a double pointed cannula. The sleeves serve as adapters that provide a bayonet socket which is fitted into another bayonet socket. The arrangement is used with a sample holder which has steps formed in an end to receive a peg that holds the arrangement together during use. As viewed, the sleeves of the cannula can easily move and expose the needle after use when it is contaminated Moreover, the arrangement requires the provision for a specially designed sample holding device to accommodate the sleeves and even with this fairly complex combination, the needle is not destroyed after use.

In the U.S. Pat. No. 4,366,544, to Wardlaw, patentee describes a hypodermic syringe which has provision for preventing more than one use and rendering the needle inoperative. According to the Wardlaw patent, a mechanism is mounted on the syringe which, after administering the injection, is manipulated to bend the needle of the syringe at right angles to the needle and concurrently retract it from its normally projecting position to a second position in which it is housed in a containment area. The retraction is accomplished by twisting a cap around a post so that the needle is permanently deformed and wrapped around the post. While protection of the needle point and destruction of the needle is provided with the mechanism, significant torque is required to twist the cap to urge the needle around the post to destroy and house it The amount of torque necessary to accomplish the wrapping and housing can exceed the strength of the various plastic parts.

Capping arrangements such as shown in Lemelson, U.S. Pat. No. 4,273,123; Karmen et al, U.S. Pat. No. 3,747,812; and Cuu, U.S. Pat. No. 4,634,428, all involve an ancillary cap over the cannula to bend or distort the metal. Similarly, the U.S. patent to Koening, U.S. Pat. No. 3,893,608, discloses a syringe that is fitted onto a cover to distort it through the placement of a post surrounding by an annular ring.

SUMMARY OF THE INVENTION

According to the present invention, I have found that after use of a hypodermic syringe, the disposition of the cannula in a hollow housing with a means to draw the cannula into the housing (preferably around a reel fitted in the housing) can enable the user to simultaneously destroy the cannula, store it and prevent accidental contact with the sharp point of the needle. After the syringe has been used, the reel is turned to draw the cannula into the housing and wrap it around the reel so that the cannula is destroyed and the point is stored within the housing When drawn into the housing and wrapped, I have further found that a positive indication of complete enclosure of the sharp point is provided by the feel and sound of the point snapping against the inside of the housing which indicates that the syringe is safe to be disposed of without potential injury. The hypodermic syringe and the housing is preferably formed of molded styrene, polycarbonates, polyamides or polyethylene.

BRIEF DESCRIPTION OF THE DRAWINGS

FIG. 1 is a perspective view of an embodiment of the hypodermic syringe of the present invention in which the cannula can be used and then destroyed and stored;

FIG. 2 is a cross-sectional view of an embodiment of the invention taken along the line 2—2 of FIG. 3 (following the cannula) in which a cannula having one point is disposed within a housing and through a reel;

FIG. 3 is a cross-sectional view of the embodiment shown in FIG. 2. In this view, the syringe has been turned −90° from the FIG. 2 view;

FIG. 4 is an enlarged fragmentary view of the reel shown in FIG. 3. In this view, the cannula has been wrapped about the reel, destroyed and stored within the housing;

FIGS. 5 and 6 are of the same embodiment, except that the cross sections are offset from each other by 90°.

Figure 5:
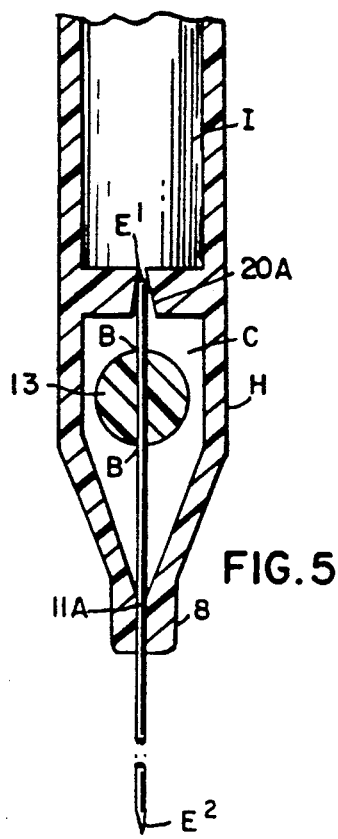
FIGS. 5 and 6 are cross-sectional views of another embodiment of the present invention. In this embodiment, the end of the cannula is detachably disposed within a bottom wall of the hypodermic syringe and through a reel.
Figure 6:
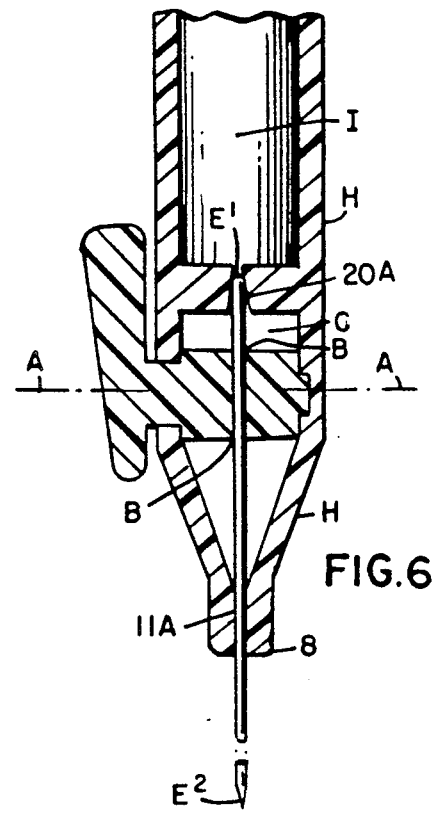
Figure 7:
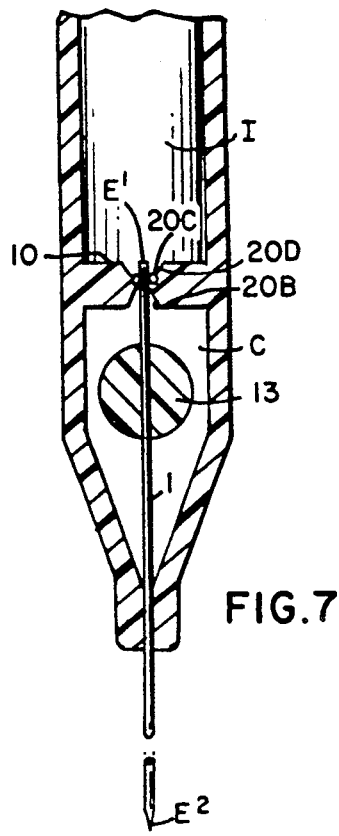
Figure 8:
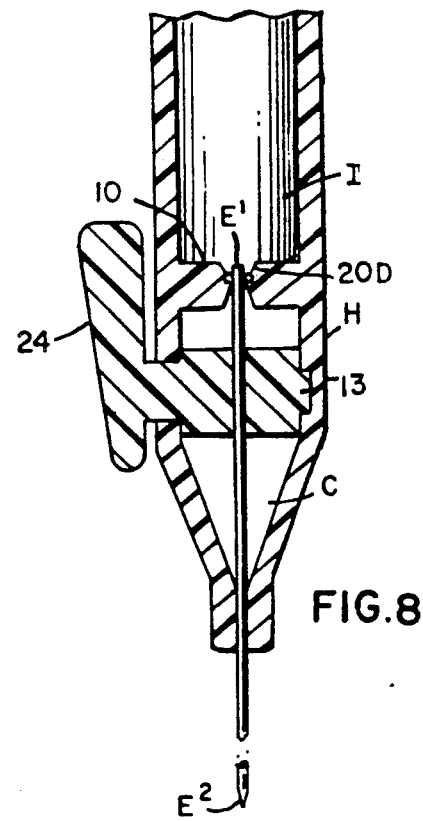

The embodiments shown in FIGS. 7 and 8 are similar to the embodiment shown in FIGS. 5 and 6, except that the blunt end of the cannula is seated in the bottom wall of the hypodermic syringe with a sealing means. Again, one cross section is offset from the other by 90°.

DESCRIPTION OF THE PREFERRED EMBODIMENTS

Referring now to FIG. 1, a cannula 1 is shown together with a hypodermic syringe 2. A plunger 4 is disposed within the transparent barrel 6, as is well known. The lower end of the hypodermic syringe includes a reel that is rotatably disposed inside a housing H (and shown in enlarged cross-sectional views in FIGS. 2 to 8). A handle 24 is integrally attached to the reel so that twisting the handle 24 will turn the reel and cause cannula 1 to be withdrawn through an aperture in a nose 8 of the housing H for destruction and storage.

Referring to FIGS. 2, 3 and 4, the cannula 1 is shown having two ends (herein called a receiving end $E^1$ and a dispensing end or point $E^2$). Part of the cannula 1 is disposed in a hollow housing H. The nose 8 of the housing H has the general shape of a nipple with an opening 11A to receive the cannula 1. An upper end 4 of the housing H is formed beneath a bottom wall 10 of the hypodermic syringe which also forms the bottom of the interior I of the syringe.

The cannula 1 is slidably disposed in the aperture 11A in the nose 8 and extends outwardly therefrom for use in injecting medications. Another portion of the cannula 1 is fixedly disposed within a throughhole 13A that is formed in reel 13. Such fixed disposition of cannula 1 can be accomplished by many means which can include the application of adhesive or simply molding the reel 13 about the cannula 1. Reel 13 is rotatably disposed within the housing H and rotates about an axis A—A which is preferably at right angles to the cannula 1 so that when the reel 13 is turned, it bends at point B and then wraps around the reel 13 (as shown in FIG. 4). Reel 13 is surrounded by a containment area C. Since cannula 1 is slidably disposed within aperture 11A, as the point $E^2$ is retracted into a containment area C in the housing H it is safely stored.

The interior I of the hypodermic syringe is in fluid flow communication with a lumen in the cannula 1 by means of an opening 20 disposed in the bottom wall 10. The opening 20 has a step adjacent the reel 13 to receive an O-ring 21 that surrounds it and urges against the reel 13 to prevent leakage into the spaces between the reel 13 and the interior of the housing H. Upon application of pressure to plunger 4, the medication will be urged into the lumen of cannula 1 to flow out of point $E^2$ of cannula 1. On the other hand, when fluids such as blood are to be withdrawn from a patient, the withdrawal of plunger 4 from the interior I of the hypodermic syringe will cause the blood flow into point $E^2$ and emerge at end $E^1$ to flow into the interior I of the hypodermic syringe. In this embodiment, the end $E^1$ of the cannula 1 is shown to be flush with the outside of the reel 13 to enable reel 13 to be turned easily about its axis. In other embodiments, however, the flush disposition of end $E^1$ relative to reel 13 may not be necessary, as will be seen in later embodiments.

As shown in FIG. 3, reel 13 is fitted in housing H so that the end with the handle 24 passes through a side wall and the other end is rotatably disposed in the opposite side wall. A step 13B is formed on reel 13 to provide for a space between reel 13 and containment area C for storage of the cannula 1.

As shown in FIG. 4, the containment area C provides space for the cannula 1 when it is wound upon reel 13. Point $E^2$ is safely stored within containment area C and cannot be touched after the cannula 1 is wound. At the same time, the O-ring 21 continues to urge against the portion of the reel 13 having the larger diameter to prevent the seepage of fluids.

As shown in FIG. 3, the cannula 1 is bent at point B at an angle necessary to place end $E^1$ beneath opening 20 in the bottom wall 10. Bending the cannula 1 at the predetermined angle enables the O-ring 21 to cover the area around cannula 1 where it emerges from the reel 13. The angle that the cannula 1 is bent is not critical so long as the end $E^1$ is disposed beneath the opening 20 and the O-ring 21. The longitudinal axis of the cannula 1 is at right angles to the axis of rotation A-A of the reel 13.

Referring now to FIGS. 5 and 6, another embodiment of the invention is shown. In this embodiment, the cannula 1 extends into a generally conically shaped opening 20A having a very narrow apex angle. The end $E^1$ of the cannula 1 is snugly force fit into the opening 20A (which is drawn somewhat exaggerated in order to show the conical shape). The essential feature, however, is that the cannula 1 is detachably removable from the opening 20A and will not allow the flow of fluids from the interior I of the syringe into the containment area C while the plunger 4 is being pushed. As in the previous embodiment, the point $E^2$ extends from the nose 8 of the housing H. Upon turning reel 13 about axis A, the cannula 1 will bend at points B and will wrap itself around reel 13. End $E^1$ will be drawn through opening 20A and simultaneously point $E^2$ will be drawn up into aperture 11A in the nose 8. Continued twisting of the reel 13 about its axis will eventually cause the point $E^2$ to be fully withdrawn into containment area C. When the cannula is fully withdrawn into containment area C, point $E^2$ will snap against the interior walls of containment area C, thereby giving an audible and tactile sensation that it is fully withdrawn and safely stored.

Another embodiment of the present invention is shown in FIG. 7 and 8. This embodiment is substantially the same as the one shown in FIGS. 5 and 6, except that cannula 1 extends through the opening 20B in bottom wall 10 and is detachably held in place by a small dab of adhesive 20C or with an O-ring or washer that has been snugly fitted over the end $E^1$ and will butt with an aperture 20D so as to prevent leakage into or from the interior I of the syringe. Twisting reel 13 about its axis A—A will break the adhesive bond (or remove the cannula 1 from the O-ring or washer) in opening 20B and cannula 1.

It is apparent that modifications and changes can be made within the spirit and scope of the present invention but it is my intention, however, only to be limited by the scope of the appended claims.

As my invention, I claim:

1. A hypodermic syringe, said syringe including a barrel with a housing disposed at one end thereof and a plunger disposed within said barrel and a cannula with a point, said syringe being characterized in that a portion of the cannula is disposed within said housing and a portion is disposed externally of said housing and that the housing has an aperture formed therein, said cannula being slidably disposed within said aperture relative to said housing and further characterized in that rotational means is disposed within said housing to retract the cannula into said housing and to receive and destroy it and to store the destroyed cannula; means to enable the retraction of the cannula.

2. The syringe according to claim 1 wherein said housing is hollow and has internal walls whereby when said point is fully retracted through said aperture into said housing, the point snaps against said internal walls to provide sensory indications that it is fully withdrawn.

3. The syringe according to claim 1 wherein said means is a reel having an axis of rotation.

4. The device according to claim 3 wherein the axis of rotation of said reel is at right angles to said cannula.

5. A hypodermic syringe, said syringe having a cannula with a point, said syringe being characterized in that a portion of the cannula is disposed within a housing having a rotational means disposed therein and a portion of the cannula is securely disposed in said rotational means whereby to enable a user to twist said rotational means and wrap the cannula around the rotational means to destroy and store said cannula; means to rotate said rotational means.

6. The syringe according to claim 5 wherein said housing is hollow and has internal walls whereby when said point is fully retracted into said housing, the point snaps against said internal walls to provide sensory indications that it is fully withdrawn.

7. The syringe according to claim 5 wherein said rotational means is a reel having an axis of rotation.

8. The device according to claim 7 wherein the axis of rotation of said rotational means is at right angles to said cannula.

9. The device according to claim 5 further including an aperture in said housing to slidably receive said cannula.

10. A medical device comprising:
    a container adapted to hold a fluid, said container having an opening at an end thereof to provide for the passage of fluids from said container to a cannula;
    a hollow housing having internal walls, a portion of said cannula being disposed within said housing and another portion extending outwardly therefrom, said housing being disposed at said end and said cannula being in fluid flow relationship with said opening;
    an aperture disposed in said housing, said cannula being slidably disposed in said aperture;
    means having an axis of rotation for retracting the outwardly extending portion of said cannula through said aperture and deforming it and then storing the deformed cannula, said means being disposed in said housing and holding said cannula relative said axis causing retraction of said cannula through said aperture and into said housing and around said means.

11. The device according to claim 10 wherein the axis of rotation of said means is at right angles to said cannula.

12. The device according to claim 10 wherein when said cannula is fully retracted into said housing it will snap against the internal walls and provide sensory indications that it is fully withdrawn.

13. A hypodermic syringe comprising:
    means to contain a fluid, said means having a bottom wall and an opening in said bottom wall to provide for the passage of fluid from said means;
    a cannula having an end disposed adjacent said bottom wall and having a point adapted to be inserted into a body;
    a hollow housing having internal walls for said cannula, said housing having an aperture at an end thereof, said housing being disposed at the end of said fluid containment means adjacent to said opening, said cannula being slidably disposed in said aperture and extending outwardly therefrom;
    means having an axis of rotation for deforming and storing the deformed cannula, said means being disposed in said housing and holding said cannula relative said axis the rotation of said means about said axis causing retraction of said cannula into said housing and around said means to store and deform it.

14. The syringe according to claim 13 further including sealing means disposed in said bottom wall around said aperture and adjacent said deforming and storing means.

15. The syringe according to claim 13 wherein the axis of rotation of said means is at right angles to said cannula.

16. The device according to claim 13 wherein when said point is fully retracted into said housing, the point snaps against said internal walls to provide sensory indications that it is fully withdrawn.

17. A disposable device for the use, destruction and storage of a cannula, said device comprising:
    a cannula having a point and an end;
    a housing for said cannula, said housing having an opening at one end in communication with a means to hold a fluid and an aperture at the other end to slidably receive the portion of the cannula having the pointed end, the portion having the pointed end extending from said opening;
    means disposed inside said housing to hold said cannula, said means having an axis of rotation, the rotation of said means causing retraction of the pointed end of said cannula into said aperture to wrap said cannula around said means to destroy and store it;
    means to enable rotation about said axis of rotation.

18. The device according to claim 17 wherein the axis of rotation of said means is at right angles to said cannula.

19. The device according to claim 17 wherein said housing is hollow and has internal walls, whereby when said pointed end is fully retracted into said housing, it will snap against said hollows walls to provide sensory indications that it is fully withdrawn.

20. The device according to claim 17 wherein a throughhole is disposed in said means whereby to hold said cannula.

21. The device according to claim 20 wherein said cannula is fixedly disposed in said throughhole.

* * * * *